US009074180B2

(12) United States Patent
Smith et al.

(10) Patent No.: US 9,074,180 B2
(45) Date of Patent: Jul. 7, 2015

(54) CULTURE MEDIUM CONTAINING KINASE INHIBITORS, AND USES THEREOF

(75) Inventors: Austin Gerard Smith, Cambridge (GB); Qi-Long Ying, Los Angeles, CA (US)

(73) Assignee: THE UNIVERSITY COURT OF THE UNIVERSITY OF EDINBURGH, Edinburgh (GB)

( * ) Notice: Subject to any disclaimer, the term of this patent is extended or adjusted under 35 U.S.C. 154(b) by 0 days.

(21) Appl. No.: 11/694,351

(22) Filed: Mar. 30, 2007

(65) Prior Publication Data

US 2008/0014638 A1 Jan. 17, 2008

(30) Foreign Application Priority Data

Mar. 30, 2006 (GB) .................................. 0606392.9
Aug. 1, 2006 (GB) .................................. 0615327.4

(51) Int. Cl.
C12N 5/0735 (2010.01)

(52) U.S. Cl.
CPC .......... *C12N 5/0606* (2013.01); *C12N 2500/90* (2013.01); *C12N 2501/115* (2013.01); *C12N 2501/727* (2013.01)

(58) Field of Classification Search
CPC ............... C12N 5/0018; C12N 5/0606; C12N 2500/00; C12N 2500/09
USPC ........................... 435/325, 353, 404, 405, 455
See application file for complete search history.

(56) References Cited

U.S. PATENT DOCUMENTS

| 6,271,436 B1 | 8/2001 | Piedrahita et al. | |
|---|---|---|---|
| 2002/0045260 A1* | 4/2002 | Hung et al. .................... | 435/368 |
| 2002/0188963 A1 | 12/2002 | Loring | |
| 2005/0037492 A1* | 2/2005 | Xu et al. ........................ | 435/366 |
| 2006/0083711 A1 | 4/2006 | Berry et al. | |
| 2008/0066197 A1 | 3/2008 | Ying et al. | |

FOREIGN PATENT DOCUMENTS

| EP | 0695351 | | 12/1999 | |
|---|---|---|---|---|
| EP | 1 726 640 A1 | | 11/2006 | |
| WO | WO 95/06716 | | 3/1995 | |
| WO | WO 00/15764 | * | 3/2000 | ............... C12N 5/00 |
| WO | WO 03/073843 | | 9/2003 | |
| WO | WO 03/095628 | | 11/2003 | |
| WO | WO 03/095628 A2 | * | 11/2003 | ............... C12N 5/00 |
| WO | WO 2005/039486 A2 | | 5/2005 | |
| WO | WO 2005/085427 | | 9/2005 | |
| WO | WO 2005/094830 A1 | | 10/2005 | |
| WO | WO 2006/026473 | | 3/2006 | |
| WO | WO 2006/135824 A1 | | 12/2006 | |
| WO | WO 2007/062243 | | 5/2007 | |
| WO | WO 2007/136465 A2 | * | 11/2007 | ........... A61K 31/159 |

OTHER PUBLICATIONS

Kobayashi et al, Eur. J. Physiol. 439:455-462, 2000.*
Ryves et al, Biochem. and Biophys. Res. Comm. 290:967-972, 2002.*
Sato et al, Nature Medicine 10(1): 55-63, 2004.*
Meijer et al, Chemistry and Biology 10:1255-1266, 2003.*
Force et al, Circulation 109:1196-1205, 2004.*
Cline et al, Diabetes 51:2903-2910, 2002.*
Jiang et al, Nature 418:41-49, 2002.*
Great Britain Search Report issued in GB0706239.1, dated Jul. 30, 2007.
Bennett et al., *J. Biol. Chem.* 277:30998-31004 (2002).
Bertrand et al., *J. Mol. Biol.* 333:393-407 (2003).
Bradley et al., *Nature* 309:255-256 (1984).
Davies et al., *Biochem. J.* 351:95-105 (2000).
Downey et al., *J. Biol. Chem.* 271:21005-21011 (1996).
European Search Report for GB0606392.9 dated Jul. 18, 2006.
European Search Report for GB0615327.4 dated Nov. 29, 2006.
Ring et al., *Diabetes* 52:588-595 (2003).
Sato et al., *Nat. Med.* 10:55-63 (2004).
Schaffer et al., *Gene* 302:73-81 (2003).
Smith et al., *Nature* 336:688-90 (1988).
Wan et al., *Chem. Biol.* 11:247-259 (2004).
Wang et al., *Oncogene* 25:43-50 (2006).
Zhang et al., *Bioorg. Med. Chem. Letters* 10:2825-2828 (2000).
Alonso et al., "GSK-3 inhibitors: Discoveries and developments," *Curr. Med. Chem.* 11(6):755-763 (2004).
English et al., "Pharmacological inhibitors of MAPK pathways," *Trends Pharmacol. Sci.* 23(1): 40-45 (2002).
Hetman et al., "ERK1/2 antagonizes glycogen synthase kinase-3beta-induced apoptosis in cortical neurons," *J. Biol. Chem.* 277(51):49577-49584 (2002).
International Search Report as issued in related International Application No. PCT/GB2007/001163, dated Oct. 9, 2007.
Meijer et al., "Pharmacological inhibitors of glycogen synthase kinase 3," *Trends Pharmacol. Sci.* 25(9):471-480 (2004).
Paling et al., "Regulation of embryonic stem cell self-renewal by phosphoinositide 3-kinase-dependent signaling," *J. Biol. Chem.* 279(46): 48063-48070 (2004).

(Continued)

*Primary Examiner* — Kevin Hill
(74) *Attorney, Agent, or Firm* — Finnegan, Henderson, Farabow, Garrett & Dunner, LLP.

(57) ABSTRACT

Pluripotent cells are maintained in a self-renewing state in serum-free culture medium comprising a MEK inhibitor, a GSK3 inhibitor and, optionally, an antagonist of an FGF receptor. Pluripotent cells are also maintained in a self-renewing state in serum-free culture medium comprising a MEK inhibitor and an antagonist of an FGF receptor.

14 Claims, 5 Drawing Sheets

(56) References Cited

OTHER PUBLICATIONS

Quevedo et al., "Two different signal transduction pathways are implicated in the regulation of initiation factor 2B activity in insulin-like growth factor-1-stimulated neuronal cells," *J. Biol. Chem.* 275(25): 19192-19197 (2000).
Brook et al., Proc. Natl. Acad. Sci., USA 94:5709-5712 (1997).
Buehr et al., Phil. Trans. R. Soc. Lon. B 358:1397-1402 (2003).
Chen et al., Proc. Natl. Acad. Sci USA 103(46):17266-17271 (2006).
Durcova-Hills et al., Stem Cells 24:1441-1449 (2006).
Frame et al., Biochem. J. 359:1-16 (2001).
Gabay et al., Neuron 40:485-499 (2003).
Huang et al., Cell Biol. Int. 31:1079-1088 (2007).
Kunath et al., Development 134:2895-2902 (2007).
McWhir et al., Nat. Genetics 14:223-226 (1996).
Niwa et al., Genes Dev. 12:2048-2060 (1998).
Niwa et al., Nat. Genet. 24:372-376 (2000).
Resnick et al., Nature 359:550-551 (1992).
Smith, Annu. Rev. Cell Dev. Biol. 17:435-462 (2001).
Stavridis et al, Development 134:2889-2894 (2007).
Vallier et al., J. Cell Sci. 118:4495-4509 (2005).
Xu et al., Nat. Methods 2(3):185-190 (2005).
Baharvand et al., "Generation of new human embryonic stem cell lines with diploid and triploid karyotypes." Develop Growth Differ. 2006; 48:117-28.
Brenin et al., "Rat embryonic stem cells: a progress report." Transplant Proc. May 1997; 29:1761-5.
Brons et al., "Derivation of pluripotent epiblast stem cells from mammalian embryos." Nature 2007; p. 1-6 (e-published Jun. 27, 2007; published in print as Nature 448:191-5).
Buehr et al., "Rapid loss of Oct-4 and pluripotency in cultured rodent blastocysts and derivative cell lines." Biol Reprod. Jan. 2003; 68:222-9.
Chambers et al., "Functional expression cloning of Nanog, a pluripotency sustaining factor in embryonic stem cells." Cell. May 2003; 113:643-55.
Charreau et al., "Transgenesis in rats: technical aspects and models." Transgenic Res. Jul. 1996; 5:223-34.
Chen et al., "Self-renewal of embryonic stem cells by a small molecule." Proc Natl Acad Sci U S A. Nov. 2006; 103:17266-71.
Dattena et al., "Lambing rate using vitrified blastocysts is improved by culture with BSA and hyaluronan." Mol Reprod Dev. Jan. 2007; 74:42-7.
Doetschman et al., "Establishment of hamster blastocyst-derived embryonic stem (ES) cells." Dev Biol. May 1988; 127:224-7.
Duesbery et al., "Anthrax lethal factor causes proteolytic inactivation of mitogen-activated protein kinase kinase." J Appl Microbiol. Aug. 1999; 87:289-93.
Dvorak et al., "Cell mixing during the early development of mouse aggregation chimera." Int J Dev Biol. Aug. 1995; 39:645-52.
Evans et al., "Establishment in culture of pluripotential cells from mouse embryos." Nature. Jul. 1981; 292:154-6.
Fändrich et al., "Preimplantation-stage stem cells induce long-term allogeneic graft acceptance without supplementary host conditioning." Nat Med. Feb. 2002; 8:171-8.
Gardner et al., "Reflections on the biology of embryonic stem (ES) cells." Int J Dev Biol. Apr. 1997; 41:235-43.
Gordon et al., "Genetic transformation of mouse embryos by microinjection of purified DNA." Proc Natl Acad Sci U S A. Dec. 1980; 77:7380-4.
Gu et al., "Orphan nuclear receptor GCNF is required for the repression of pluripotency genes during retinoic acid-induced embryonic stem cell differentiation." Mol Cell Biol. Oct. 2005; 25:8507-19.
Holm et al., "High bovine blastocyst development in a static in vitro production system using SOFaa medium supplemented with sodium citrate and myo-inositol with or without serum-proteins." Theriogenology. Sep. 1999; 52:683-700.
Iannaccone et al., "Pluripotent embryonic stem cells from the rat are capable of producing chimeras." Dev Biol. May 1994; 163:288-92.
Iannaccone et al., "Correction." Dev. Biol. 1997; 185:124-125.
Kozlova et al., "The influence of HLIF on the development of bovine embryonic stem cell outgrowth." Proceedings of the 5th Annual Meeting of the International Society for Stem Cell Research, Abstract MON-255, 2007; p. 130-131.
Li et al., "Comparative analysis of development-related gene expression in mouse preimplantation embryos with different developmental potential." Mol. Repr. Dev. 2005; 72:152-160.
Lonergan et al., "Effect of protein supplementation and presence of an antioxidant on the development of bovine zygotes in synthetic oviduct fluid medium under high or low oxygen tension." Theriogenology. Jun. 1999; 51:1565-76.
Mak et al., "Reactivation of the paternal X chromosome in early mouse embryos." Science. Jan. 30, 2004; 303:666-9.
Martin., "Isolation of a pluripotent cell line from early mouse embryos cultured in medium conditioned by teratocarcinoma stem cells." Proc Natl Acad Sci U S A. Dec. 1981; 78:7634-8.
Matsuda et al., "STAT3 activation is sufficient to maintain an undifferentiated state of mouse embryonic stem cells." EMBO J. Aug. 1999; 18:4261-9.
Matsui et al., "Derivation of pluripotential embryonic stem cells from murine primordial germ cells in culture." Cell. Sep. 1992; 70:841-7.
Mitsui et al., "The homeoprotein Nanog is required for maintenance of pluripotency in mouse epiblast and ES cells." Cell. May 30, 2003; 113:631-42.
Murray et al., "Exploitation of Kestrel to identify NDRG family members as physiological substrates for SGK1 and GSK3." Biochem J. Dec. 2004; 384:477-88.
Nichols et al., "Rat and mouse epiblasts differ in their capacity to generate extraembryonic endoderm." Reprod Fertil Dev. 1998; 10:517-25.
Nichols et al., "Formation of pluripotent stem cells in the mammalian embryo depends on the POU transcription factor Oct4." Cell. Oct. 1998; 95:379-91.
Niwa, "How is pluripotency determined and maintained?." Development. Feb. 2007; 134:635-46.
Niwa et al., "Self-renewal of pluripotent embryonic stem cells is mediated via activation of STAT3." Genes Dev. 1998; 12:2048-2060.
Niwa et al., "Interaction between Oct3/4 and Cdx2 determines trophectoderm differentiation." Cell. Dec. 2, 2005; 123:917-29.
Notarianni et al., "Derivation of pluripotent, embryonic cell lines from the pig and sheep." J Reprod Fertil Suppl. 1991; 43:255-60.
Okamoto et al., "Epigenetic dynamics of imprinted X inactivation during early mouse development." Science. Jan. 30, 2004; 303:644-9.
Pashai et al., "Derivation and long-term maintenance of bovine stem cell lines." Proceedings of the 5th Annual Meeting of the International Society for Stem Cell Research, Abstract TUE-248, 2007; p. 220.
Prelle et al., "Establishment of pluripotent cell lines from vertebrate species—present status and future prospects." Cells Tissues Organs. 1999; 165 (3-4) :220-36.
Rastan et al., "X-chromosome deletions in embryo-derived (EK) cell lines associated with lack of X-chromosome inactivation." J Embryol Exp Morphol. Dec. 1985; 90:379-88.
Rathjen et al., "Differentiation inhibiting activity is produced in matrix-associated and diffusible forms that are generated by alternate promoter usage." Cell. Sep. 21, 1990; 62:1105-14.
Richings et al., "DNA demethylation promotes expansion and supports long-term maintenance of bovine embryonic stem cells in vitro." Proceedings of the 5th Annual Meeting of the International Society for Stem Cell Research, Abstract TUE-247, 2007; p. 220.
Rodríguez et al., "Effects of human versus mouse leukemia inhibitory factor on the in vitro development of bovine embryos." Theriogenology. Mar. 15, 2007; 67:1092-5.
Ruhnke et al., "Long-term culture and differentiation of rat embryonic stem cell-like cells into neuronal, glial, endothelial, and hepatic lineages." Stem Cells. 2003; 21:428-36.
Saito et al., "Bovine embryonic stem cell-like cell lines cultured over several passages." Roux's Arch Dev. Biol. 1992; 201:134-141.
Schulze et al., "Derivation, maintenance, and characterization of rat embryonic stem cells in vitro." Methods Mol Biol. 2006; 329:45-58.
Silva et al., "Establishment of histone h3 methylation on the inactive X chromosome requires transient recruitment of Eed-Enx1 polycomb group complexes." Dev Cell. Apr. 2003; 4:481-95.

(56) References Cited

OTHER PUBLICATIONS

Sukoyan et al., "Isolation and cultivation of blastocyst-derived stem cell lines from American mink (Mustela vison)." Mol Reprod Dev. Dec. 1992; 33:418-31.
Tervit et al., "Successful culture in vitro of sheep and cattle ova." J Reprod Fertil. Sep. 1972; 30:493-7.
Tesar et al., "New cell lines from mouse epiblast share defining features with human embryonic stem cells." Nature. Jul. 12, 2007; 448:196-9.
Thomson et al., "Embryonic stem cell lines derived from human blastocysts." Science. Nov. 6, 1998; 282:1145-7.
Vassilieva et al., "Establishment of SSEA-1- and Oct-4-expressing rat embryonic stem-like cell lines and effects of cytokines of the IL-6 family on clonal growth." Exp Cell Res. Aug. 1, 2000; 258:361-73.
Verma et al., "Successful isolation of ESC lines from mouse blastocysts pre-treated with the demethylating agent, 5-azacytadine." Proceedings of the 5th Annual Meeting of the International Society for Stem Cell Research, Abstract WED-236, 2007; p. 309.
Voigt et al., "Pluripotent stem cells and other technologies will eventually open the door for straightforward gene targeting in the rat." Dis Model Mech. Jul. 2009; 2:341-3.
Watanabe et al., "A Rock inhibitor permits survival of dissociated human embryonic stem cells." Nat Biotechnol. Jun. 2007; 25:681-6.
Wiles et al., "Embryonic stem cell development in a chemically defined medium." Exp Cell Res. Feb. 25, 1999; 247:241-8.
Wutz et al., "A shift from reversible to irreversible X inactivation is triggered during ES cell differentiation." Mol Cell. Apr. 2000; 5:695-705.
Yamamura et al., "The production of chimeric rats and their use in the analysis of the hooded pigmentation pattern." Dev. Genet. 1981; 2:131-146.
Ying et al., "Defined conditions for neural commitment and differentiation." Methods Enzymol. 2003; 365:327-41.
Ying et al., "BMP induction of Id proteins suppresses differentiation and sustains embryonic stem cell self-renewal in collaboration with STAT3." Cell. Oct. 31, 2003; 115:281-92.
Ying et al., "Conversion of embryonic stem cells into neuroectodermal precursors in adherent monoculture." Nat Biotechnol. Feb. 2003; 21:183-6.
Zhan et al., "Conservation and variation of gene regulation in embryonic stem cells assessed by comparative genomics." Cell Biochem Biophys. 2005; 43:379-405.
Zwaka et al., "A germ cell origin of embryonic stem cells?." Development. Jan. 2005; 132:227-33.
Smith, *Stem Cell Biology*, Chapter 10: Embryonic Stem Cells, pp. 205-230 (2001), Cold Spring Harbor Laboratory Press, Cold Spring Harbor, NY.
Klimanskaya et al., "Human Embryonic Stem Cell Lines Derived From Single Blastomeres," Advanced Cell Technology, vol. 444, Nov. 23, 2006 (6 pages).
Yamanaka, "Signaling Maintaining Pluripotency in ES Cells," Protein Nucleic Acid Enzyme, 2004, vol. 49, No. 6, p. 704-709.
Nakagawa et al., "Mechanism for Maintaining Pluripotency in Embryonic Stem Cells and Inner Cell Mass," Protein Nucleic Acid Enzyme, 2005, vol. 50, No. 6, p. 546-550.
Niwa et al., "Molecular Mechanism for Maintain Self-Renewal of Human ES Cells," Cell Technology, 2004, vol. 23, No. 11, p. 1260-1263.
Finlay et al., "Glycogen Synthase Kinase-3 Regulates IGFBP-1 Gene Transcription through the Thymine-Rich Insulin Response Element," BMC Molecular Biology, 2004, vol. 5:15., p. 1-13.
Japanese Patent Application 2009-502219, Official Action dated Oct. 8, 2013.
Burdon et al., Suppression of SHP-2 and ERK Signaling Promotes Self-Renewal of Mouse Embyonic Stem Cells; Dev. Biol., vol. 210, No. 1, (1999) pp. 30-43.

\* cited by examiner

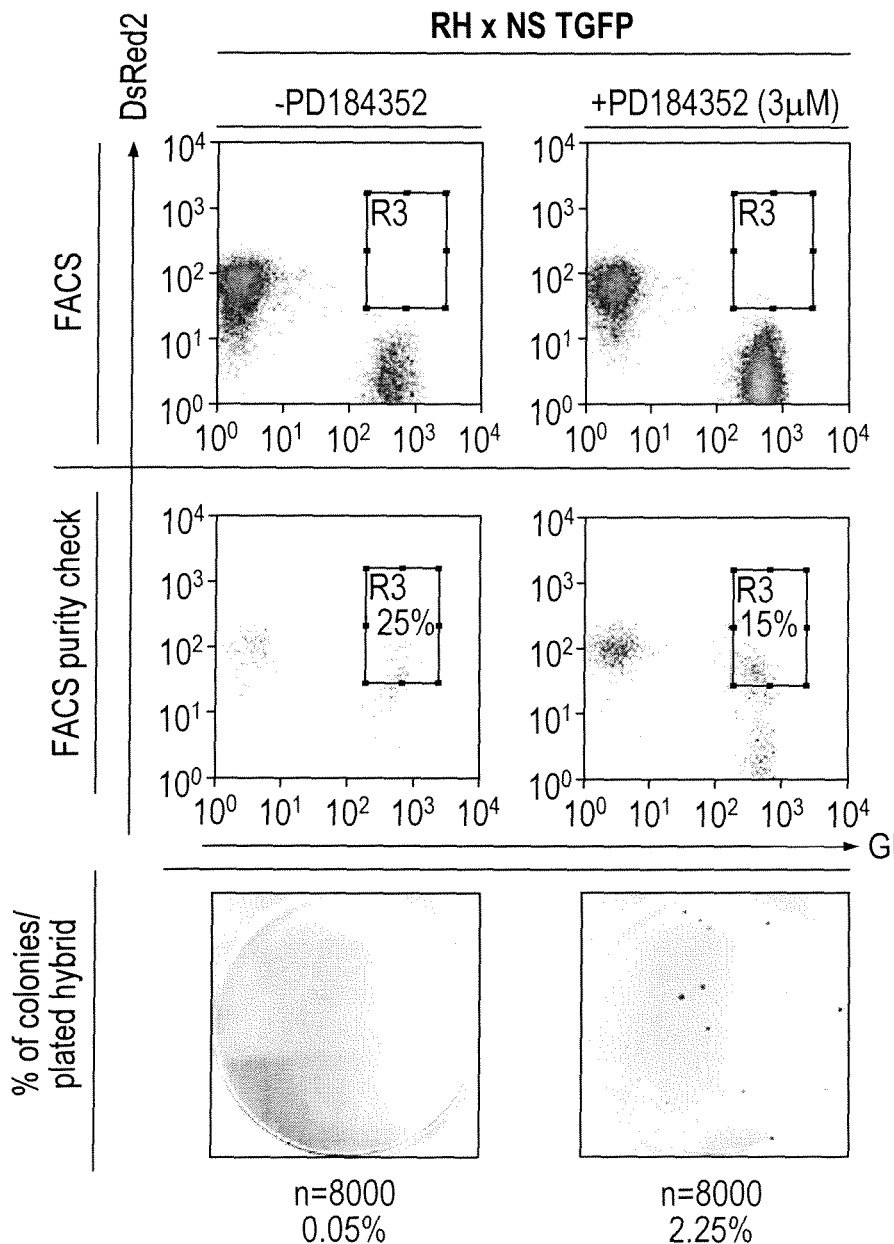

| PD184352 treatment | + (3μM) | - |
|---|---|---|
| Hybrid pair | RH-NSTGFP | RH-NSTGFP |
| n FACS Sorted cells | 8000 | 8000 |
| FACS Purity | 15% | 20% |
| n true double positive cells | 1200 | 1600 |
| n hybrid colonies | 27 | 1 |
| % of Colonies/ Plated hybrids | 2.25% | 0.05% |

Fig. 2
Figure 2B
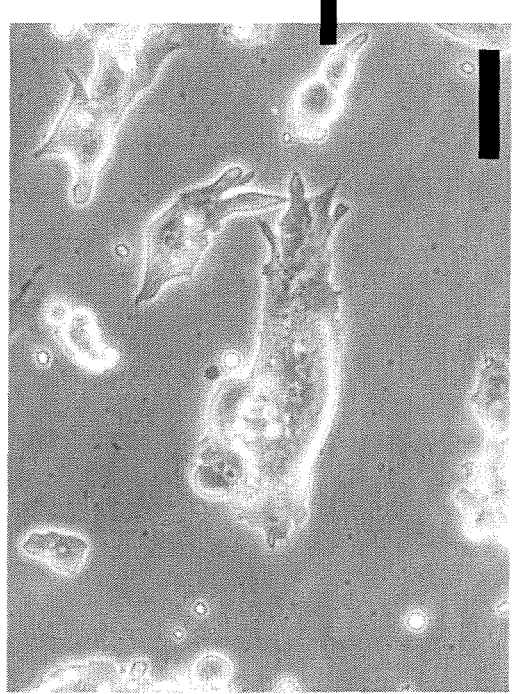
Figure 2A

CULTURE MEDIUM CONTAINING KINASE INHIBITORS, AND USES THEREOF

This application claims the benefit under 35 U.S.C. §119 of Great Britain Application No. 0606392.9, filed Mar. 30, 2006, and Great Britain Application No. 0615327.4, filed Aug. 1, 2006.

The present invention relates to maintenance of a self renewing phenotype in pluripotent stem cells. The methods and compositions provided are suitable for culturing and isolating pluripotent stem cells such as embryonic stem (ES) cells, especially mammalian, including rat, mouse, bovine, ovine, porcine, and human, stem cells. In particular this invention relates to self-renewing cultures of rat, mouse and human pluripotent cells and to methods and compositions therefor.

The establishment and maintenance of in vitro pluripotent stem cell cultures in the presence of medium containing serum and Leukaemia Inhibitory Factor (LIF) is well known (Smith et al. (1988) Nature 336: 688-90). Such methods have been used to maintain pluripotent embryonic stem (ES) cells from "permissive" strains of mice over many passages. Maintenance and self renewal of pluripotent stem cell cultures is further supported where the stem cells are cultured in the presence of feeder cells or extracts thereof, usually mouse fibroblast cells. Under such conditions it is possible to maintain human ES cells in a pluripotent state over many passages in culture.

In many cases ES cells can only be maintained, or are best maintained, using medium that contains serum or serum extract, and hence is undefined, or using cell culture conditions that require the presence of other cells, such as the fibroblast feeder cells used to maintain human ES cells. But any undefined component, whether in the medium or produced by e.g. the feeder cells, potentially interferes with or hinders research into ES cell propagation and differentiation. This prevents development of good manufacturing practices for therapeutic and other applications of ES cells and their progeny. Some defined ES cell media are known but alternative and/or improved defined media are needed.

In prior applications by the applicants, WO-A-03/095628 and a later as yet unpublished application, culturing pluripotent stem cells, such as ES cells, in serum-free media comprising (1) agonists of gp130 (e.g. LIF) and (2) agonists of the TGF-β superfamily (e.g. BMP4) or Id signalling pathways is used to promote self renewal of the stem cells for multiple passages. In the presence of gp130 signalling, an agonist of the TGF-β superfamily or the Id signalling pathway surprisingly provided a self renewal stimulus rather than a pro-differentiation signal. Nevertheless, ever improved efficiencies in maintaining pluripotent cells in a self renewing state and media for transferring pluripotent cells away from feeder cells or away from feeder-conditioned medium is desired.

Sato N, et al, Nat. Med. Jan. 10, 2004(1) pp 55-63 describe the effects of a Glycogen Synthase Kinase 3 (GSK3) inhibitor, 6-bromoindirubin-3'-oxime, on mouse and human ES cells in serum containing medium. These effects, however, were observed only over a very short time frame, too short for firm conclusions to be drawn, and the influence of unknown factors in the undefined media used in that study may be significant. The inventors of the present invention have tried but failed to repeat the results, and have in fact found effects opposite to those described.

For preparation of ES cell culture media it is desired to provide individual media components in as pure a form as possible. However, most media components are cytokines the purity of which is compromised by the need to manufacture them in cellular systems and then remove potential contaminants from the production broth. Another problem with some cytokines is that they have a narrow range of concentration over which they are effective and non-toxic. Media components which have a broader range and/or are less toxic at higher concentrations would be highly useful. Cytokines can also have limited stability in storage, and more stable media components are sought.

An object of the invention is to overcome or at least ameliorate problems in the art, e.g. to provide alternative or improved, methods of culturing and culture media suitable for pluripotent stem cells, which are capable of supporting self-renewal of said stem cells for many passages. A further object of the invention is to provide an alternative culturing system that permits maintenance of a pluripotent stem cell culture in vitro until differentiation of the cells can be induced in a controlled manner. A still further object of the invention is to provide methods and compositions that enhance the derivation and isolation of pluripotent stem cells and facilitate their derivation and isolation from organisms refractory to ES cell isolation or from which pluripotent stem cells have not yet been isolated.

DETAILED DESCRIPTION

In accordance with the present invention, pluripotent stem cells, such as ES cells, are cultured in medium comprising a MEK inhibitor and a GSK3 inhibitor, or a MEK inhibitor and an antagonist of an FGF receptor. In some embodiments, the medium is serum-free. In some embodiments, the medium comprises a MEK inhibitor, a GSK3 inhibitor and an antagonist of a FGF receptor (e.g. a small molecule GSK3 inhibitor and a small molecule MEK inhibitor and a small molecule FGFR antagonist). Self renewal of the stem cells for multiple passages is thereby promoted. Hence, inhibition of GSK3 and MEK, inhibition of MEK and FGF receptor signaling, or inhibition of GSK3, MEK and FGF receptor signalling in the pluripotent cells provides a self renewal stimulus.

The invention has a number of applications. A combination of GSK3 and MEK, MEK and FGFR or GSK3, MEK and FGFR inhibition can be used to grow pluripotent cells, especially ES cells, and, where they have been derived or grown on feeder cells, to adapt pluripotent cells, especially ES cells, to grow without feeder cells or a layer of feeder cells, often referred to as feeders or feeder cells. A method of expanding stem cells in culture comprises culturing the cells in the presence of a GSK3 inhibitor and a MEK inhibitor, in the presence of a MEK inhibitor and an antagonist of an FGF receptor. In some embodiments, the method comprises culturing the cells in the presence of a GSK3 inhibitor, a MEK inhibitor and an antagonist of a FGF receptor. Culture medium can be prepared containing one or more GSK3 inhibitors and MEK inhibitors, one or more MEK inhibitors and FGFR antagonists and, optionally, one or more MEK inhibitors, GSK3 inhibitors and FGFR antagonists. ES cells can be derived using GSK3 inhibitors and MEK inhibitors, using MEK inhibitors and FGFR antagonists, or using GSK3 inhibitors, MEK inhibitors and FGFR antagonists.

According to a first aspect of the present invention, inhibition of GSK3 and MEK, or inhibition of all of GSK3 and MEK and a FGF receptor, in a pluripotent cell is used to promote self-renewal of the cell.

BRIEF DESCRIPTION OF THE DRAWINGS

FIGS. 1A-1E show analysis of the effect of PD184352 in the formation of pluripotent ES-NS hybrid colonies. (FIGS.

1A-1C)—FACS analysis for red and green fluorescence of RH×NS TGFP fusions. (FIG. 1A) Fusion mixture 24 hours after PEG treatment; (FIG. 1B) Purity check of FACS sorted hybrids gated in A. (FIG. 1C) Hybrids sorted in A were plated and the formed colonies were scored as percentage of colonies per plated hybrid. These scores take into account the purity of the FACS sorted cells. (FIG. 1D) Summary of data. (FIG. 1E) Examples of hybrid colony morphology.

FIG. 2 shows mouse ES cells derived and maintained according to the invention and shows high efficiency of chimera contribution by these ES cells. FIG. 2A shows ES cells derived and maintained in N2B27 medium with the three inhibitors and no serum, no feeder cells, and no LIF present from the very beginning of the culture. FIG. 2B shows high efficiency of chimera contribution.

Figures 1D, 1E:
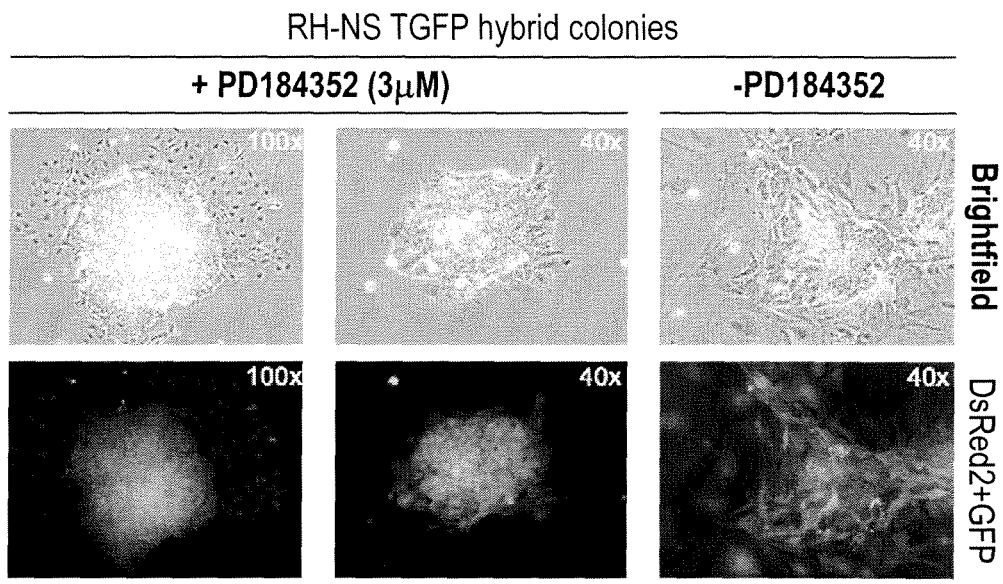
Figure 3:
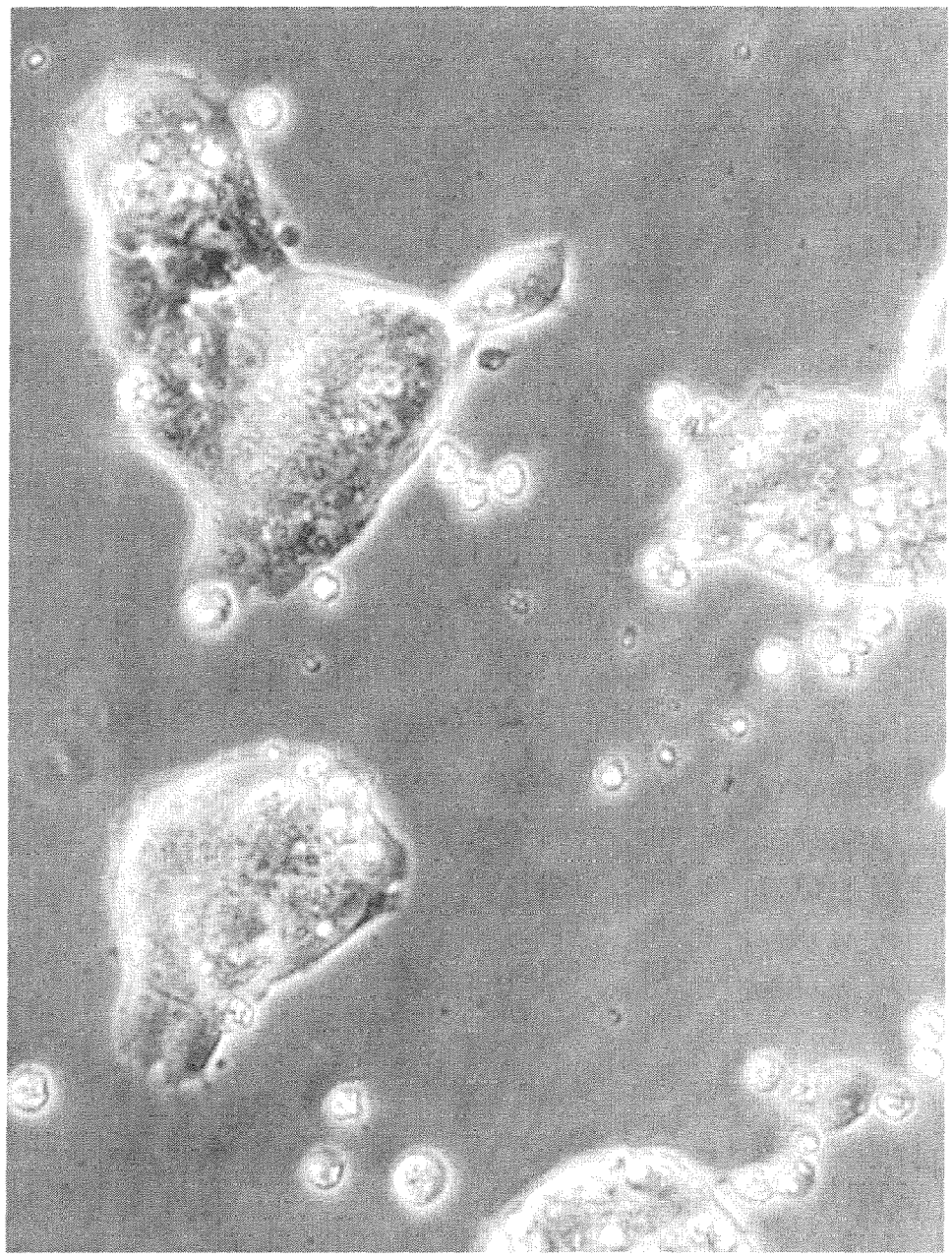
FIG. 3 shows passage 4 mouse ES cells grown in accordance with the invention. Mouse ES cells were grown from single sorted LIF receptor knock-out ES cell in N2B27 medium plus 3 µM CHIR99021, 1 µM PD184352, and 2.5 µM SU5402.
Figure 4:
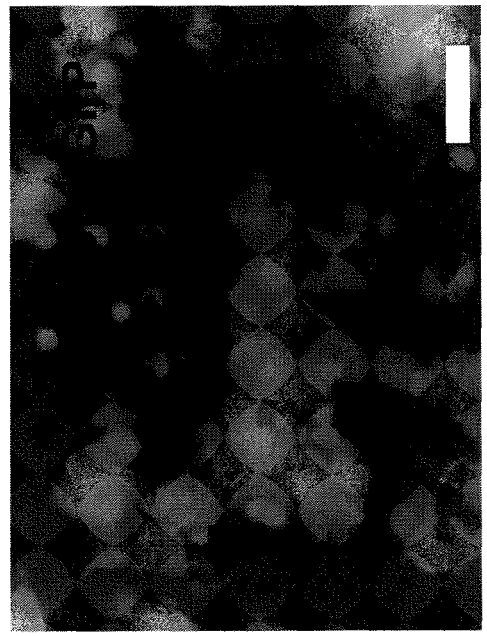
FIG. 4 shows mouse ES cells, grown in accordance with the invention, are Oct4 positive. From sorted single Oct4GIP ES cells, passage 5 total 29 days in culture. The culture medium is N2B27 plus 3 µM CHIR99021, 1 µM PD184352 and 2.5 µM SU5402. The GFP is driven by Oct4 promoter, so the GFP positive cells are Oct4 positive ES cells. Bar=100 µM.
Figure 4:
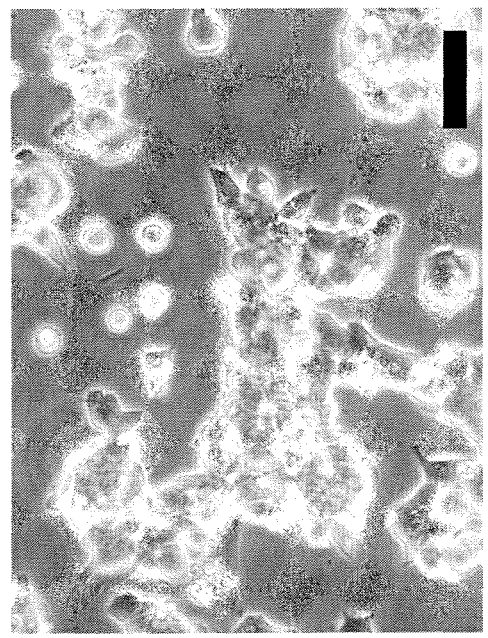

Reference to pluripotent cells includes but is not limited to reference to embryonic stem (ES) cells. Characteristic properties of pluripotent cells, including ES cells, include the expression of multiple genes associated with the pluripotent stage of development, the ability to differentiate into cells representative of any and all tissue types present in the source animal, the ability to contribute to chimeras and, particularly, the ability to contribute to the germ line of chimeras. For example true pluripotent cells, such as ES cells, would be expected to express many, if not all, of the pluripotency-associated genes Nanog, Oct4, FGF4, Sox-2 and alkaline phosphatase. In particular, expression of Nanog, Oct4 and Sox-2 is widely regarded as providing a definitive initial indication that a cell is an ES cell. Germ line transmission in chimeras and the ability to generate teratomas or teratocarcinomas comprising differentiated cells from all three primary germ layers (i.e. endoderm, mesoderm and ectoderm) are also widely regarded as definitive indications of a cell being an ES cell.

Reference to GSK3 inhibition refers to inhibition of one or more GSK3 enzymes. Thus a GSK3 inhibitor can inhibit one member, several members or all members of the family of GSK3 enzymes. The family of GSK3 enzymes is well-known and includes but is not limited to GSK3-α and GSK3-β. A number of variants have been described (see e.g. Schaffer et al.; Gene 2003; 302(1-2): 73-81). In specific embodiments GSK3-β is inhibited. GSK3-α inhibitors are also suitable, and in general inhibitors for use in the invention inhibit both. A wide range of GSK3 inhibitors are known including but not limited to the inhibitors CHIR 98014, CHIR 99021, AR-AO144-18, TDZD-8, SB216763 and SB415286. Other inhibitors are known and useful in the invention. In addition, the structure of the active site of GSK3-β has been characterised and key residues that interact with specific and non-specific inhibitors have been identified (Bertrand et al.; J Mol Biol. 2003; 333(2): 393-407). This structural characterisation allows additional GSK inhibitors to be readily identified.

The inhibitors of certain embodiments are specific for GSK3-β and GSK3-α, substantially do not inhibit erk2 and substantially do not inhibit cdc2. In some embodiments the inhibitors have at least 100 fold, at least 200 fold, or at least 400 fold selectivity for human GSK3 over mouse erk2 and/or human cdc2, measured as ratio of $IC_{50}$ values; here, reference to GSK3 $IC_{50}$ values refers to the mean values for human GSK3-β and GSK3-α. Good results have been obtained with CHIR 99021 and CHIR 98014, which are both specific for GSK3. Examples of GSK3 inhibitors are described in Bennett C, et al, J. Biol. Chem., vol. 277, no. 34, Aug. 23, 2002, pp 30998-31004 and in Ring D B, et al, Diabetes, vol. 52, March 2003, pp 588-595. Suitable concentrations for use of CHIR 99021 are in the range 0.01 to 100, for example 0.1 to 20, or 0.3 to 10 micromolar.

GSK3 inhibition can also be conveniently achieved using RNA mediated interference (RNAi). Typically, a double-stranded RNA molecule complementary to all or part of a GSK3 gene is introduced into pluripotent cells, thus promoting specific degradation of GSK3-encoding mRNA molecules. This post-transcriptional mechanism results in reduced or abolished expression of the targeted GSK3 gene. Suitable techniques and protocols for achieving GSK3 inhibition using RNAi are known.

Reference to a MEK inhibitor herein refers to MEK inhibitors in general. Thus, reference to a MEK inhibitor refers to any inhibitor of a member of the MEK family of protein kinases, including MEK1, MEK2 and MEK3. Reference is also made to MEK1, MEK2 and MEK3 inhibitors. A MEK inhibitor can inhibit one member, several members or all members of the family of MEK kinases. Examples of suitable MEK inhibitors, already known in the art, include but are not limited to the MEK1 inhibitors PD184352 and PD98059, inhibitors of MEK1 and MEK2 U0126 and SL327, and those discussed in Davies et al (2000) (Davies S P, Reddy H, Caivano M, Cohen P. Specificity and mechanism of action of some commonly used protein kinase inhibitors. Biochem J. 351, 95-105). In particular, PD184352 has been found to have a high degree of specificity and potency when compared to other known MEK inhibitors. Other MEK inhibitors and classes of MEK inhibitors are described in Zhang et al. (2000) Bioorganic & Medicinal Chemistry Letters; 10:2825-2828.

Inhibition of MEK kinases can also be conveniently achieved using RNA-mediated interference (RNAi). Typically, a double-stranded RNA molecule complementary to all or part of a MEK gene is introduced into pluripotent cells, thus promoting specific degradation of MEK-encoding mRNA molecules. This post-transcriptional mechanism results in reduced or abolished expression of the targeted MEK gene. Suitable techniques and protocols for achieving MEK inhibition using RNAi are known.

A number of assays for identifying kinase inhibitors, including GSK3 inhibitors and MEK inhibitors, are known. For example, Davies et al (2000) describe kinase assays in which a kinase is incubated in the presence of a peptide substrate and radiolabelled ATP. Phosphorylation of the substrate by the kinase results in incorporation of the label into the substrate. Aliquots of each reaction are immobilised on phosphocellulose paper and washed in phosphoric acid to remove free ATP. The activity of the substrate following incubation is then measured and provides an indication of kinase activity. The relative kinase activity in the presence and absence of candidate kinase inhibitors can be readily determined using such an assay. Downey et al. (1996) J Biol Chem.; 271(35): 21005-21011 also describes assays for kinase activity which can be used to identify kinase inhibitors.

Reference to an antagonist of fibroblast growth factor (FGF) receptor (FGFR) refers to a polypeptide or small molecule or other antagonist of a FGF receptor, typically inhibiting FGFR1 and/or FGFR2. Thus, a FGF receptor antagonist can be an antagonist of one, several or all members of the FGF receptor family, including but not limited to FGFR1, FGFR2, FGFR3 and FGFR4. Members of the FGF receptor family typically comprise three immunoglobulin-like domains and present a region of acidic amino acids (the acidic box) which can participate in the binding of a member of the FGF family to a FGF receptor. In some cases, molecules comprising only two immunoglobulin-like domains can also function as FGF receptors. A number of FGFR antagonists are known, including but not limited to SU5402 and PD173074. Suitable concentrations of SU5402 are in the micromolar range, such as from 0.1-20 µM. Some embodiments use concentrations in the range 0.5-10 µM, especially in the range 1-5 µM. We have found that PD173074 can substitute for SU5402 and is fully effective at about 100-fold lower concentrations, consistent with its higher affinity for the FGF receptor. Thus, suitable concentrations for PD173074 are in the range 1-200 nM. In some embodiments the concentration is in the range 5-100 nM, especially in the range 10-50 nM. It is also known to inhibit FGR receptor signalling by transgene expression of a dominant negative mutant FGF receptor. In embodiments of the invention a small molecule antagonist and not a transgenic based antagonism is used.

Suitable assays for identifying antagonists of FGF receptors are known. For example, a cell line in which signalling via a FGF receptor activates expression of a reporter gene can be used to assess the activity of a potential antagonist.

It has advantageously been found that the use of a MEK inhibitor in combination with a GSK3 inhibitor and optionally also an antagonist of the FGF receptor improves the propagation of ES cells.

In some embodiments between around 0.1 µM and around 25 µM MEK inhibitor are used. In other embodiments, between around 0.1 µM and around 5 µM MEK inhibitor are used, for example from 0.2 µM to 2 µM.

In some embodiments media according to the invention comprise 0.8 µM PD184352, 3 µM CHIR99021 and/or 3 µM SU5402. In other embodiments the medium comprises 0.8 µM PD184352, 3 µM CHIR99021 and 3 µM SU5402, for example in N2B27 medium. The concentration of SU5402 can be optimized to suit different pluripotent cell lines, typically in the range 1-5 µM (e.g. 2 µM).

In examples below, we have cultured mouse ES cells in the presence of a GSK3 inhibitor together with a MEK inhibitor and, in a specific example, an antagonist of the FGF receptor to promote self renewal. In other specific examples, a method of promoting self-renewal of mouse pluripotent cells in culture comprises inhibiting GSK3 and MEK or inhibiting GSK3, MEK and an FGF receptor.

Optionally, activating gp130 downstream signalling can also be employed to further enhance the promotion of self renewal by inhibiting GSK3 and MEK. Molecules that activate gp130 downstream signalling are sometimes referred to as gp130 activators or gp130 agonists. Activation of one or more gp130 downstream signalling pathways can be achieved by use of a cytokine acting through gp130, for example a cytokine or other agonist of the LIF receptor. Cytokines capable of acting through gp130, and thus of activating gp130 signal transduction, include but are not limited to LIF, ciliary neurotrophic factor (CNTF), cardiotrophin, oncostatin M, IL-6 plus sIL-6 receptor, hyper IL-6 and IL-11. Suitable cytokines include mimetics, fusion proteins or chimaeras that can bind to and/or activate signalling though gp130. The role of cytokines acting through gp130 in the presence of serum is well established, but the capacity of those cytokines to sustain undifferentiated cells in the absence of serum is limited.

An advantage of the invention is that in the presence of a GSK3 inhibitor, a MEK inhibitor and, optionally, an antagonist of the FGF receptor, pluripotent cells can be grown in defined medium. A particular advantage associated with using the combination of a GSK3 inhibitor, a MEK inhibitor and an antagonist of the FGF receptor is that it is not necessary for the medium to contain other growth factors, such as insulin, N2B27, or a gp130 agonist (e.g. LIF). The present invention therefore enables alternative and/or improved culture of ES cells in medium that is free of serum, serum extract, feeder cells and feeder cell extract.

Purported embryonic stem cells have been reported from a number of mammalian sources including mouse (Bradley et al (1984) Nature 309: 255-56), American mink (Mol Reprod Dev (1992) December; 33(4):418-31), pig and sheep (J Reprod Fertil Suppl (1991); 43:255-60), hamster (Dev Biol (1988) May; 127(1):224-7) and cow (Roux Arch Dev Biol (1992); 201: 134-141). Specific examples herein use mouse and human ES cells and also rat cell from primary outgrowths. It will be appreciated that the methods and compositions of the present invention are suitable for adaptation to culturing of other mammalian pluripotent cell cultures, thus including primate, especially human, rodent, especially mouse and rat, and avian pluripotent stem cells, especially ES cells.

A second aspect of the invention provides a method of culture of pluripotent cells, especially ES cells, so as to promote self renewal, comprising maintaining the cells in medium containing:
  a) an inhibitor of GSK3; and
  b) an inhibitor of MEK.

In some embodiments, the method comprises maintaining the cells in medium containing:
  a) an inhibitor of GSK3;
  b) an inhibitor of MEK; and
  c) an antagonist of an FGF receptor.

Methods of the invention can be used generally for growing pluripotent cells, including growing ES cells in medium which is free of serum and free of serum extract, which cells have previously been passaged in the presence of serum or serum extract. Such methods can also be carried out in the absence of feeder cells and/or feeder cell extracts. For example, culture of ES cells can be carried out comprising the steps of:
  a) maintaining the ES cells in a pluripotent state in culture, optionally on a layer of feeder cells;
  b) passaging the ES cells at least once;
  c) withdrawing the serum or the serum extract from the medium and withdrawing the feeder cells (if present), so that the medium is free of feeder cells, serum and serum extract; and
  d) subsequently maintaining ES cells in a pluripotent state in the presence of an inhibitor of GSK3, a MEK inhibitor and, optionally, an FGFR antagonist.

Further optionally, the cells can be maintained in a pluripotent state in the presence of a MEK inhibitor, a GSK3 inhibitor and an activator of a gp130 downstream signalling pathway.

The present invention also provides a method of obtaining a transfected population of ES cells, comprising:
  a) transfecting ES cells with a construct encoding a selectable marker;
  b) plating the ES cells;
  c) culturing the ES cells in the presence of a MEK inhibitor, a GSK3 inhibitor and, optionally, an FGFR antagonist; and
  d) selecting for cells that express the selectable marker.

Further optionally, the cells are cultured in the presence of a MEK inhibitor, a GSK3 inhibitor and an activator of a gp130 downstream signalling pathway.

The selectable marker may encode antibiotic resistance, a cell surface marker or another selectable marker as described e.g. in EP-A-0695351, and, in some embodiments, comprises a nucleotide sequence encoding the selectable marker operatively linked to a promoter which preferentially expresses the selectable marker in desired cells.

In a further embodiment, the present invention provides a method of culture of pluripotent, especially ES, cells, comprising the steps of transferring an individual cell to a culture vessel, such as an individual well on a plate, and culturing the cell in the presence of a GSK3 inhibitor, a MEK inhibitor and, optionally, an FGFR antagonist, so as to obtain a clonal population of pluripotent, especially ES, cells, all of which are progeny of a single cell. Optionally, the cells may also be cultured in the presence of an activator of gp130 downstream signalling pathways.

Once a stable, homogenous culture of ES cells is obtained, the culture conditions can be altered to direct differentiation of the cells into one or more cell types selected from ectodermal, mesodermal or endodermal cell fates. Addition of, or withdrawal of cytokines and signalling factors, can enable the derivation of specific differentiated cell populations at high efficiency. Differentiation of an ES cell towards a non-neuroectodermal fate may be achieved by maintaining the ES cell in the presence of a cytokine acting through gp130, a MEK inhibitor and a GSK3 inhibitor and then withdrawing the cytokine whilst maintaining the GSK3 inhibitor and MEK inhibitor and/or adding a further signalling molecule capable of directing differentiation. Alternatively, the cells may be maintained in the presence of a MEK inhibitor and a GSK3 inhibitor and then differentiation directed by withdrawing one or both of the inhibitors and/or adding a signalling molecule capable of directing differentiation. The methods described above all optionally include the step of obtaining and/or isolating a differentiated cell which is the product of the process.

Further aspects of the invention provide for cell culture media. One medium is for self-renewal of pluripotent, especially ES, cells, the medium comprising an inhibitor of GSK3, an inhibitor of MEK and, optionally, an FGFR antagonist. The medium may also optionally comprise an activator of a gp130 downstream signalling pathway. Another medium of the invention is a stem cell culture medium, comprising an inhibitor of GSK3, a MEK inhibitor and, optionally, an FGFR antagonist. All media can further comprise basal medium. In some embodiments, all media are free of an agonist of gp130, and are for example free of LIF.

The invention provides medium that is free of serum and serum extract. One such medium comprises:
a) basal medium;
b) a MEK inhibitor;
c) a GSK3 inhibitor; and
d) an iron-transporter; wherein the medium is optionally free of serum and serum extract.

In some embodiments the medium also comprises an FGFR antagonist. The medium may also optionally comprise an activator of a gp130 downstream signalling pathway.

Medium for pluripotent stem cells, especially rat or mouse cells, may be free of serum and of gp130 agonists and comprises a MEK inhibitor, a GSK3 inhibitor, and an antagonist of an FGF receptor. Substitutions of media components can be made as described herein.

Basal medium is medium that supplies essential sources of carbon and/or vitamins and/or minerals for the cells. The basal medium is generally free of protein and incapable on its own of supporting self-renewal of cells. The iron transporter provides a source of iron or provides the ability to take up iron from the culture medium. Suitable iron transporters include transferrin and apotransferrin. In some embodiments the medium further comprises one or more of insulin or insulin-like growth factor and albumin (which can be recombinant) or albumin substitute, and is free of feeder cells and feeder cell extract. The medium may also comprise an inhibitor of apoptosis or any other component that promotes the maintenance of pluripotent cells in culture.

A particular medium of the invention comprises MEK inhibitor, GSK3 inhibitor, insulin, albumin and transferrin, with or without additional basal medium. In this medium, LIF can be optionally included and can be substituted by other activators of gp130 signalling. Thus, in some embodiments the medium comprises the gp130 receptor binding cytokine, LIF, suitable concentrations of which are generally between 10 U/ml and 1000 U/ml, for example between 50 U/ml and 500 U/ml, e.g. in the region of 100 U/ml. The GSK3 and MEK inhibitors are generally as described herein in more detail.

The invention further provides a method of deriving a pluripotent cell from a blastocyst, comprising:
a) obtaining a blastocyst;
b) culturing the blastocyst in the presence of a MEK inhibitor, a GSK3 inhibitor and, optionally, an antagonist of an FGF receptor, to obtain an inner cell mass;
c) dissociating the inner cell mass;
d) isolating a cell or cells from the dissociated inner cell mass; and
e) culturing the isolated cell or cells in the presence of a MEK inhibitor, a GSK3 inhibitor and, optionally, an antagonist of an FGF receptor.

Optionally, the isolated cell or cells are cultured in the presence of a MEK inhibitor, a GSK3 inhibitor and an activator of gp130 downstream signalling. An antagonist of an FGF receptor may also be present.

In some embodiments, the method comprises culturing the blastocyst in LIF, for example for a period of from 2 to 4 days. In some embodiments the isolated cell or cells are cultured in serum free medium. Typically, the cells are replated as clumps. In some embodiments the blastocyst is also cultured in serum free medium, optionally in the absence of an agonist of the BMP receptor.

In some embodiments of the invention, the culture of cells is carried out in an adherent culture, which may be promoted by the inclusion of a cell adhesion protein on culture substrate. In some embodiments the culture of pluripotent cells according to the invention is in monolayer culture, though it is optional for cells to be grown in suspension culture or as pre-cell aggregates; cells can also be grown on beads or on other suitable scaffolds such as membranes or other 3-dimensional structures.

Culture medium used in some of the examples of the invention also comprises serum albumin. This can be used in purified or preferably recombinant form, and if in a recombinant form this has the advantage of absence of potential contaminating factors, cytokines etc. The culture medium does not need to contain serum albumin and this component can be omitted or replaced by another bulk protein or by a synthetic polymer (polyvinyl alcohol) as described by Wiles et al.

In some embodiments the medium is one that is fully defined. This medium does not contain any components which are undefined, that is to say components whose content is unknown or which may contain undefined or varying factors that are unspecified. An advantage of using a fully defined medium is that efficient and consistent protocols for culture and subsequent manipulation of pluripotent cells can be derived. Further, it is found that maintenance of cells in a pluripotent state is achievable with higher efficiency and greater predictability and that when differentiation is induced in cells cultured using a defined medium the response to the differentiation signal is more homogenous than when undefined medium is used.

The invention also provides concentrates which can be used as additives for culture medium, and kits of components, for preparation of culture medium, the resultant medium being in accordance with the invention. One kit of the invention comprises first and second containers, the first containing a MEK inhibitor and the second containing a GSK3 inhibitor. In some embodiments, the kit comprises a third container containing an antagonist of a FGF receptor. The kit may also, optionally, comprise a further container containing an activator of gp130 downstream signalling. In some embodiments the kits are formulated so that the contents of each container can be added to culture medium so as to obtain a culture medium of the invention. Thus, in some embodiments the kits contain concentrated stock solutions of their respective components.

Methods of the invention also include a method of obtaining a differentiated cell comprising culturing a pluripotent cell as described and allowing or causing the cell to differentiate, wherein the cell contains a selectable marker which is capable of differential expression in the desired differentiated cell compared with other cell-types, including pluripotent stem cells, whereby differential expression of the selectable marker results in preferential isolation and/or survival and/or division of the desired differentiated cells. The selectable marker may be expressed in the desired differentiated cells but not expressed in other cell types, or the level of expression may differ between desired differentiated cells and other cell types, thereby allowing selection for expression of the selectable marker. The differentiated cell can be a tissue stem or progenitor cell, and may be a terminally differentiated cell.

Generally also, the invention extends to a cell obtained by following any of the methods of the invention described herein. Cells of the invention can be used in assays for drug discovery. Cells of the invention may also be used for cell therapy, and thus a method of the invention comprises using a combination of inhibition of MEK and inhibition of GSK3 and, optionally, antagonism of FGF signalling to derive and/or maintain pluripotent cells, deriving cells for cell therapy therefrom and using those cells in cell therapy. Optionally, the combination is used in the absence of an activator of gp130 downstream signalling.

Further aspects of the invention relate to the use of inhibition of MEK and an FGF receptor, optionally in combination with inhibition of GSK3 for promoting self-renewal of pluripotent cells. We have found that the combination of a MEK inhibitor and an antagonist of an FGF receptor is effective in supporting the growth of pluripotent cells in serum-free medium in the absence of added cytokines or growth factors.

Accordingly, a further aspect of the invention provides a culture medium, comprising a MEK inhibitor and an antagonist of an FGF receptor. The MEK inhibitor and the antagonist of an FGF receptor are as described in relation to other aspects of the invention. Similarly, the culture medium may further comprise additional components or factors as described herein in relation to other aspects of the invention.

Yet another aspect of the invention provides use of a MEK inhibitor and an antagonist of an FGF receptor in manufacture of a culture medium for pluripotent cells.

The invention also provides methods for culturing pluripotent cells and obtaining transfected populations of pluripotent cells, which may be conveniently carried out as described for other aspects of the invention. Accordingly, a further aspect of the invention provides a method of culture of pluripotent cells so as to promote self renewal, comprising maintaining the cells in medium comprising a MEK inhibitor and an antagonist of an FGF receptor.

A related aspect of the invention provides a method of culture of pluripotent cells, comprising the steps of:
a) maintaining the ES cells in a pluripotent state in culture, optionally on feeder cells,
b) passaging the ES cells at least once;
c) withdrawing serum or serum extract (if present) from the medium and withdrawing the feeder cells (if present), so that the medium is free of feeder cells, serum and serum extract; and
d) subsequently maintaining ES cells in a pluripotent state in the presence of a MEK inhibitor and an inhibitor of an FGF receptor.

A further aspect of the invention provides a method of obtaining a transfected population of ES cells, comprising:
a) transfecting ES cells with a construct encoding a selectable marker;
b) plating the ES cells;
c) culturing the ES cells in the presence of a MEK inhibitor and an FGF receptor antagonist and
d) selecting for cells that express the selectable marker.

Also provided is a cell culture medium that is free of serum and serum extract and comprises:
a) basal medium;
b) a MEK inhibitor;
c) an antagonist of an FGF receptor; and
d) an iron-transporter.

The combination of a MEK inhibitor and an antagonist of an FGF receptor is also useful for deriving new pluripotent cell lines. Accordingly, a further aspect of the invention provides a method of deriving a pluripotent cell from a blastocyst, comprising:
a) obtaining a blastocyst;
b) culturing the blastocyst in the presence of a MEK inhibitor and an antagonist of an FGF receptor, to obtain an inner cell mass;
c) dissociating the inner cell mass;
d) isolating a cell or cells from the dissociated inner cell mass; and
e) culturing the isolated cell or cells in the presence of a MEK inhibitor and an antagonist of an FGF receptor.

The invention also includes kits comprising first and second containers, the first containing a MEK inhibitor and the second containing an antagonist of an FGF receptor. The kit may also comprise other containers and/or components as described herein.

Further aspects of the invention provide use of a MEK inhibitor and an antagonist of an FGF receptor in promoting self-renewal of pluripotent stem cells, especially pluripotent stem cells expressing Nanog. A related aspect provides a method of expanding a stem cell population, comprising culturing the stem cells in the presence of a MEK inhibitor and an antagonist of an FGF receptor.

A number of advantages of the invention are described above or apparent. Cell culture components may be identified which are relatively non-toxic and cell permeable. The MEK inhibitors, GSK3 inhibitors and FGFR antagonists used in specific embodiments of the invention can be purified easily, especially compared to, say, purification of protein cytokines. Recombinant proteins can be expensive to make and the small molecule medium components may be more cheaply produced and more stable in storage, with a wider effective concentration range.

Specific embodiments set out below used a combination of CHIR 99021, PD184352 and, optionally, SU5402 in a serum-free, fully defined medium and gave improved self renewal of mouse ES cells with very little differentiation. It is occasionally reported when culturing ES cells in the presence of BMP that there is some neurogenesis. This was not seen in the examples of the invention.

The invention is now further described in specific examples, illustrated by drawings. In the examples the term 2i medium or 2i is used to indicate medium comprising a MEK inhibitor and an antagonist of an FGF receptor. The term 3i medium or 3i is used to indicate medium comprising a MEK inhibitor, a GSK3 inhibitor and an antagonist of an FGF receptor.

EXAMPLES

GSK-3β Inhibitors, MEK Inhibitors, Culture Medium and ES Cell Self-Renewal

Mouse and human ES cells were grown under various conditions, using N2B27 medium unless otherwise stated and in the presence or absence of the GSK-3β inhibitors CHIR99021, AR-A0144-18, SB216763 and SB415286 and the MEK inhibitor PD184352.

Preparation of N2B27 Medium:

N2 100× stock solution. For 10 ml: mix 1 ml insulin (final concentration 2.5 mg/ml) with 1 ml apo-transferrin (final concentration 10 mg/ml), 0.67 ml BSA (final concentration 5 mg/ml), 33 µl progesterone (final concentration 2 µg/ml), 100 µl putrescine (final concentration 1.6 mg/ml), 10 µl sodium selenite (final concentration 3 µM) and 7.187 ml DMEM/F12. Store at 4° C. and use within 1 month.

DMEM/F12-N2 medium: to 100 ml of DMEM/F12, add 1 ml of N2 100× stock solution. The final concentration of each component of N2 in the DMEM/F12 medium is: insulin, 25 µg/ml; apo-transferrin, 100 µg/ml; progesterone, 6 ng/ml; putrescine, 16 µg/ml; sodium selenite, 30 nM; BSA 50 µg/ml. Store at 4° C. and use within 1 month.

Neurolbasal/B27 medium: to 100 ml of Neurolbasal™ Medium, add 2 ml of B27 and 0.5-1 ml of 200 mM L-glutamine. Store at 4° C. and use within 1 month.

N2B27 medium: mix DMEM/F12-N2 medium with Neurolbasal/B27 medium in the ratio of 1:1. Add β-mercaptoethanol to a final concentration of 0.1 mM from the 0.1M stock. Store at 4° C. and use within 1 month.

Example 1

In serum-free medium a MEK inhibitor plus a GSK-3β inhibitor was sufficient to sustain mouse ES cell self-renewal in both (1) N2B27 medium, and (2) fully defined medium (DMEM/F12-N2)—data not shown. Self renewal of ES cells was improved further in medium containing a MEK inhibitor, a GSK-3β inhibitor and LIF (data not shown).

Example 2

It was shown that PD184352, an inhibitor of MEK, increases the levels of Nanog in ES cells (data not shown). In addition, it was shown that Nanog −/− ES cells treated with PD184352 failed to show enhancing of ES cell self-renewal (data not shown). In fact, these cells differentiated. This demonstrated that the enhancing of ES self-renewal phenotype by PD184352 is mediated by Nanog.

The effect of PD184352 in reprogramming was also investigated by determining the conversion of NS cells to pluripotency in the context of cell fusion.

RH ES cells, which express constitutively the dsRed fluorescent protein and hygromycin resistance, were fused to foetal derived Neural Stem cells (NS TGFP) that express the fusion protein TauGFP linked via an IRES to puromycin resistance. In one of the fusions RH cells were treated for 3 days prior and after fusion with 3 µM PD184352. In the control no PD184352 was added. Treated and untreated primary hybrids were sorted 24 hours after fusion and then plated (FIG. 1A-C). Hygromycin and puromycin selection were added to the ES medium 3 days later. Colonies expressing dsRed2 and GFP fluorescence and exhibiting ES cell morphology were scored (FIGS. 1D and E). Results showed that PD184352 enhanced ES-NS hybrid colony formation by 45-fold. Interestingly, the percentage of hybrid colonies formed per plated hybrid in PD184352 treated RH cells was just 2-fold lower compared to Nanog overexpressing ES cells (2.25% vs 4%). This result shows that PD184352 not only enhances ES cell self-renewal but also enhances reprogramming in the cell fusion context. This effect is likely to be mediated by the increased levels of Nanog in treated RH cells. Accordingly, if Nanog is endogenously expressed then the MEK inhibitor can be used to upregulate Nanog and achieve associated effects, such as increased reprogramming.

Example 3

Human ES cells were cultured in media supplemented with the GSK-3 inhibitor CHIR99021 and the MEK inhibitor PD184352.

The addition of LIF to the culture media further improved propagation of the cells (data not shown).

Example 4

Mouse ES cells were cultured in media supplemented with the GSK-3 inhibitor CHIR99021 and the MEK inhibitor PD184352.

The addition of LIF to the culture media further improved propagation of the cells (data not shown).

Example 5

Mouse and human ES cells were grown in medium containing CHIR99021, PD184352 and SU5402, prepared as follows:

Concentrations of the Three Inhibitors/Antagonist:

| Compound | Initial concentration | Dilutions | Final Concentration when added to media |
|---|---|---|---|
| CHIR99021 | 10 mM Store at −20 >1 yr | Aliquot stock in 20 ul aliquots. Initial 1:10 dilution with N2B27 media = 1 mM. Store at 4° C. Add diluted stock to media at 1:333 to make 3 µM final. | 3 µM This concentration was used for all cell lines |
| PD184352 | 10 mM Store at −20 >1 yr | Aliquot stock in 10 ul aliquots. Initial 1:100 dilution in N2B27 = 1 ml of 100 uM, store at | 0.8 µM Some cell lines were grown in concentrations |

-continued

| Compound | Initial concentration | Dilutions | Final Concentration when added to media |
|---|---|---|---|
| SU5402 | 5 mM Store at −20 >1 yr | 4° C. Add to media at 1:125 for 0.8 µM final. Initial 1:10 dilution = 0.5 mM in N2B27. Add to media at 1:250 for final concentration of 2 µM | varying in the range = 0.5-1 µM 2 µM Some cell lines may need to be optimised, range = 1-5 µM |

Media

Preparation of DMEM/F12-N2 Medium

To 100 ml of DMEM/F12 (Gibco 42400-010) add 1 ml of N2 100× stock solution. The final concentration of each component of N2 in the DMEM/F12 medium is:

Insulin 25 µg/ml Putrescine 16 µg/ml Transferrin 100 µg/ml

Sodium Selenite 30 nM Progesterone 6 ng/ml BSA 50 µg/ml

Preparation of Neurobasal/B27

To 100 ml Neurobasal medium (Gibco 21103-049) add 2 ml of B27 (Gibco 17504-044) and 1-2M L-glutamine (TC stores 1:100)

Preparation of N2 B27 Medium

Mix DMEM/F12-N2 medium with Neurobasal/B27 medium at the ratio of 1:1.

The media was used to dilute all compounds and grow the cells.

The medium was used for maintenance of human ES cells and for derivation and maintenance of ES cells from 129 strain mice, and also for derivation of ES cells from the non-permissive mouse strains CBA and C56/BL6.

Example 6

Mouse ES cells were cultured in the presence of an inhibitor of the FGF receptor and a MEK inhibitor. Selective pharmacological inhibitors SU5402 and PD184352 were used to inhibit FGF receptor tyrosine kinase and activation of Erk1/2 via MEK1/2, respectively. We found that addition of either inhibitor is sufficient for robust ES cell propagation in N2B27 medium containing LIF without provision of BMP4 (data not shown). Undifferentiated cultures can be continuously passaged in these conditions while retaining expression of the pluripotency markers Oct4, Nanog, and Rex1. Neural commitment does not occur despite much lower expression of Id genes than in cultures maintained with LIF plus BMP.

ES cells plated in N2B27 medium without added LIF, conditions that normally elicit efficient neural commitment, remain Oct4 positive and Sox1 negative for several days if either SU5402 or PD184352 are added (data not shown). However, these cells invariably differentiate and/or die after passaging. To reduce potential toxic side effects we used 2.5 fold lower doses and combined the two inhibitors together. In N2B27 with 0.8 µM PD184352 plus 2 µM SU5402, some differentiation is observed initially, but ES cells persist and expand after passage (data not shown). Viability is lower and population doubling time slower in this two inhibitor (2i) condition than in the presence of ILIF, but differentiation is effectively restrained. This finding suggests that the minimal requirements for ES cell self-renewal may be to deflect differentiation signals emanating from FGF receptor and Erk signaling while avoiding compromise to cell growth and viability.

Example 7

We reasoned that reduced growth of ES cells in 2i media could be due to increased activity of glycogen synthase kinase 3 (GSK-3) consequent to release of inhibitory phosphorylation by Rsk downstream of pErk. CHIR99021 is a well-characterised highly selective small molecule inhibitor of GSK-3 that does not cross react with cyclin-dependent kinases (CDKs) at concentrations that completely block GSK-3 activity. When added to cultures in the presence of serum we found that CHIR99021 (3 µM) actually promotes differentiation, even in the presence of LIF. In serum-free N2B27 medium the differentiation response is reduced and some colonies appear morphologically Undifferentiated for several days. However, Undifferentiated cells do not persist after passaging (data not shown). Similar results were obtained with two other widely used GSK-3 inhibitors, SB216763 and SB415286, although both appeared somewhat toxic to ES cells.

However, when CHIR99021 is combined with 2i the differentiation response is lost entirely. Furthermore, CHIR99021 modulated the response to 2i such that ES cells grew as compact three dimensional colonies rather than flattened monolayers typically seen in LIF plus serum/BMP or in 2i. Differentiation was negligible in the three inhibitors (3i) and ES cells propagated rapidly. Most importantly undifferentiated colonies grew up at high efficiency after passaging (data not shown). Derivatives of two independent parental ES cell lines, E14Tg2a and CGR8 showed robust long term expansion in 3i with little or no overt differentiation. They express Oct4, Nanog and Rex1 and do not exhibit appreciable expression of lineage commitment markers, Gata4, Sox1, or brachyury (data not shown). In bulk culture ES cells expand with a comparable doubling rate in 3i as in LIF plus BMP, and the proportion of Oct4-GFP positive undifferentiated cells remains over 90% (data not shown).

Thus, 3i medium can be used to culture ES cells without differentiation in the absence of serum or added cytokines.

Example 8

A rigorous test of the sufficiency of a culture formulation to sustain ES cell self-renewal is formation of undifferentiated colonies by individual cells. After single cell deposition, cloning efficiency in N2B27 plus 3i is 25% (98/384), higher than with LIF plus BMP (11%, 23/192)—data not shown. These colonies express Oct4-GFP and are passageable as undifferentiated ES cells. Thus, medium comprising a MEK inhibitor, an inhibitor of the FGF receptor and a GSK3 inhibitor is able to sustain the formation of undifferentiated ES cell colonies derived from single cells.

Example 9

We examined whether 3i was adequate for the derivation of new ES cells directly from embryos or reflected an adaptation of established lines. Blastocysts from the permissive 129 strain were plated directly in N2B27 plus 3i on gelatin-coated plastic and cultured for 5 days. After subsequent dissociation and replating of the inner cell mass, ES cell colonies were obtained from 7 of 12 embryos. Three of these were expanded and injected into blastocysts. All gave high rates of chimaerism and germline transmission (Table 1). Subsequently we have derived multiple ES cells from C57BL/6 and non-permissive CBA and MF1 strains indicating that 3i facilitates the transition from epiblast to ES cell. We conclude that 3i liberates ES cells from requirements for exogenous LIF and BMP/serum without selection or compromise to developmental potency.

TABLE 1

Contribution of ES cells derived in 3i to chimaeras and production of germline offspring

| Cell line | No. embryos injected | No. live-born pups | No. chimaeras* | No. test-mated | No. trans-mitting* |
|---|---|---|---|---|---|
| CPS1 | 64 | 16 | 12 | 8 (5m, 3f) | 3f# |
| CPS2 | 21 | 5 | 4 | 3 (1m, 2f) | 2f# |
| CPS3 | 20 | 15 | 11 | 4 (3m, 1f) | 2m |

*Chimaerism and transmission of the 129/Ola ES cell genome detected by coat colour
ES cells assumed to be XX.

Thus, ES cells are maintained in a combination of a GSK3 inhibitor and a MEK inhibitor, a MEK inhibitor and an antagonist of an FGF receptor or, optionally, a GSK3 inhibitor, a MEK inhibitor and an antagonist of an FGF receptor and the invention also provides culture methods and media therefor.

We claim:

1. A culture medium comprising:
   a. rat embryonic stem (ES) cells;
   b. the MEK1 inhibitor PD184352 at a concentration of 0.2-2 µM;
   c. the GSK3 inhibitor CHIR99021 at a concentration of 0.3-10 µM; and
   d. the antagonist of an FGF receptor SU5402 at a concentration of 1-5 µM,
   wherein said culture medium comprising said PD184352, CHIR99021 and SU5402 supports propagation of germline competent rat ES cells.

2. The culture medium of claim 1, further comprising a gp130 agonist.

3. The culture medium of claim 2, wherein the gp130 agonist is selected from LIF, CNTF, cardiotrophin, oncostatin M, IL-6 plus sIL-6 receptor and hyper IL-6.

4. The culture medium of claim 2, wherein the gp130 agonist is selected from LIF, sIL-6R and hyper IL-6.

5. The culture medium of claim 1, comprising N2 medium and/or B27 medium.

6. The culture medium of claim 1, further comprising an iron transporter, and is free of serum and serum extract.

7. The culture medium of claim 6, further comprising an activator of a gp130 downstream signalling pathway.

8. The culture medium of claim 6, further comprising insulin, albumin and transferrin.

9. A culture medium comprising:
   a. the MEK1 inhibitor PD184352 at a concentration of 0.1-5 µM;
   b. the GSK3 inhibitor CHIR99021 at a concentration of 0.1-20 µM; and
   c. the antagonist of an FGF receptor SU5402 at a concentration of 0.5-10 µM,
   wherein said culture medium comprising said PD184352, CHIR99021 and SU5402 supports propagation of germline competent rat ES cells.

10. The culture medium of claim 9, wherein:
    a. the MEK1 inhibitor PD184352 is at a concentration of 0.2-2 µM;
    b. the GSK3 inhibitor CHIR99021 is at a concentration of 0.3-10 µM; and
    c. the antagonist of an FGF receptor SU5402 is at a concentration of 1-5 µM.

11. A method of obtaining a transfected population of rat embryonic stem (ES) cells, the method comprising:
    a) transfecting rat ES cells with a construct encoding a selectable marker;
    b) plating the rat ES;
    c) culturing the rat ES cells in a culture medium comprising:
       i. the MEK1 inhibitor PD184352 at a concentration of 0.2-2 µM;
       ii. the GSK3 inhibitor CHIR99021 at a concentration of 0.3-10 µM; and
       iii. the antagonist of an FGF receptor SU5402 at a concentration of 1-5 µM; and
    d) selecting for rat ES cells that express the selectable marker.

12. The method of claim 11, wherein the culture medium of step c) further comprises an activator of a gp130 downstream signalling pathway.

13. A method of culturing rat ES cells, the method comprising the steps of:
    a) maintaining the ES cells in a pluripotent state in culture, optionally on a layer of feeder cells;
    b) passaging the ES cells at least once;
    c) withdrawing any serum or serum extract from the medium and withdrawing any feeder cells, so that the medium is free of feeder cells, serum and serum extract; and
    d) subsequently culturing the ES cells in a culture medium comprising:
       i. the MEK1 inhibitor PD 184352 at a concentration of 0.2-2 µM;
       ii. the GSK3 inhibitor CHIR99021 at a concentration of 0.3-10 µM; and
       iii. the antagonist of an FGF receptor SU5402 at a concentration of 1-5 µM.

14. A method of expanding a rat embryonic stem (ES) cell population, the method comprising the steps of culturing the rat ES cells in a culture medium comprising:
    a. the MEK1 inhibitor PD184352 at a concentration of 0.2-2 µM;
    b. the GSK3 inhibitor CHIR99021 at a concentration of 0.3-10 µM; and
    c. the antagonist of an FGF receptor SU5402 at a concentration of 1-5 µM.

* * * * *